US006381780B1

(12) United States Patent
Nose et al.

(10) Patent No.: US 6,381,780 B1
(45) Date of Patent: May 7, 2002

(54) TABLE AND MR APPARATUS

(75) Inventors: Katsumasa Nose; Akira Izuhara, both of Tokyo (JP)

(73) Assignee: GE Yokogawa Medical Systems, Limited, Tokyo (JP)

( * ) Notice: Subject to any disclaimer, the term of this patent is extended or adjusted under 35 U.S.C. 154(b) by 0 days.

(21) Appl. No.: 09/563,640

(22) Filed: May 2, 2000

(30) Foreign Application Priority Data

Jul. 7, 1999 (JP) .......................................... 11-192657

(51) Int. Cl.[7] ................................................ A47G 13/00
(52) U.S. Cl. .................................... 5/601; 5/614; 5/943
(58) Field of Search ............................ 5/601, 614, 943, 5/600; 378/209

(56) References Cited

U.S. PATENT DOCUMENTS 4,773,637 A * 9/1988 Jarin ............................. 5/601
5,272,776 A * 12/1993 Kitamura ........................ 5/601
6,092,248 A * 7/2000 Boemmel et al. .............. 5/601
6,256,528 B1 * 7/2001 Zonneveld et al. ............ 5/601

* cited by examiner

*Primary Examiner*—Alexander Grosz
(74) *Attorney, Agent, or Firm*—Moonray Kojima

(57) ABSTRACT

In order to provide a table and an MR apparatus which allows moving of a cradle and scanning to be simultaneously performed, in a table 55 comprising a table body 57, a cradle 59 provided on the table body 57 and driving means 61 for driving the cradle 59, the driving means 61 has a hydraulic motor (i.e., a driving source utilizing fluid pressure) 69 as a driving source.

16 Claims, 3 Drawing Sheets

51
53
56
71
67
73
65
87
83
(a)
(b)
(c)
86
85
61
63
68
69
cradle 59
table body 57
55
CONTROL SECTION
91
OPER. SECTION
95
PUMP
81
82

TABLE AND MR APPARATUS

BACKGROUND OF THE INVENTION

The present invention relates to a table comprising a table body, a cradle provided on the table body and driving means for driving the cradle, and an MR (magnetic resonance) apparatus having the table.

In an MR apparatus, a table for carrying an object under study into a magnet is comprised of a table body, a cradle provided on the table body, and driving means for driving the cradle.

For a driving source of the driving means, a pulse motor is employed which, when supplied with electric pulses, is rotated by a constant angle for each input pulse.

However, when the pulse motor is driven during scanning by the MR apparatus, the input pulses give rise to noises and adversely affect a captured image.

Therefore, driving of the cradle and scanning cannot be simultaneously performed, That is, imaging cannot be performed while driving the cradle.

Thus, when an extended region is to be imaged, the scanning should be suspended to move the cradle, which leads to a problem that an imaging time per object under study is protracted.

Moreover, since the pulse motor comprises magnets and coils, it cannot be accurately driven in a high-strength magnet field.

This also affects a captured image.

Accordingly, when the pulse motor is employed, it must be disposed at a place that is not affected by the magnetic field, which leads to another problem that a mounting position for the pulse motor is restricted.

SUMMARY OF THE INVENTION

It is therefore an object of the present invention to provide a table and an MR apparatus which allows moving of a cradle and scanning to be simultaneously performed.

It is another object of the present invention to provide a table and an MR apparatus which imposes no restrictions on a mounting position for a driving source.

In accordance with a first aspect of the invention, there is provided a table comprising a table body, a cradle provided on the table body, and driving means for driving the cradle, wherein the driving means has a driving source utilizing fluid pressure.

In accordance with a second aspect of the invention, there is provided an MR apparatus having a table comprising a table body, a cradle provided on the table body and driving means for driving the cradle, wherein the driving means of the table has a driving source utilizing fluid pressure.

By employing a driving source utilizing fluid pressure as driving means for driving a cradle, noises which adversely affect a captured image are not generated during driving of the cradle.

Therefore, moving of the cradle and scanning can be simultaneously performed.

The fluid pressure may be, but is not limited to, liquid pressure or as pressure.

In addition, the driving source utilizing the fluid pressure may be, but is not limited to, a hydraulic motor, a hydraulic cylinder or an air cylinder, for example.

In accordance with a third aspect of the invention, there is provided the table as described regarding the first aspect, wherein the driving source is a hydraulic motor.

When the moving amount for a driven object is small, a hydraulic cylinder or an air cylinder is preferable because the driving means can be simplified, and when the moving amount for a driven object is large, a hydraulic motor is preferable because the driving means can be made compact.

While the fluid may be gas or liquid, liquid, which is an incompressible fluid, provides better controllability.

Therefore, in the present table and MR apparatus, a hydraulic motor is preferable for the driving source insofar as the driving means can be made compact and the driving means can provide good controllability.

In accordance with a fourth aspect of the invention, there is provided the table as described regarding the first or third aspect, wherein the driving source is made of a non-magnetic material.

In accordance with a fifth aspect of the invention, there is provided the MR apparatus as described regarding the second aspect, wherein the driving source is made of a non-magnetic material.

By making a driving source out of a non-magnetic material, it can be accurately driven even in a high-strength magnetic field, and it does not affect a captured image.

Accordingly, a mounting position for the driving source is not restricted.

Thus, the present invention can provide a table and an MR apparatus which allows moving of a cradle and scanning to be simultaneously performed.

Moreover, the present invention can provide a table and an MR apparatus which imposes no restrictions on a mounting position for a driving source.

Further objects and advantages of the present invention will be apparent from the following description of the preferred embodiments of the invention as illustrated in the accompanying drawings.

DETAILED DESCRIPTION OF THE INVENTION

First Embodiment

Figure 1:
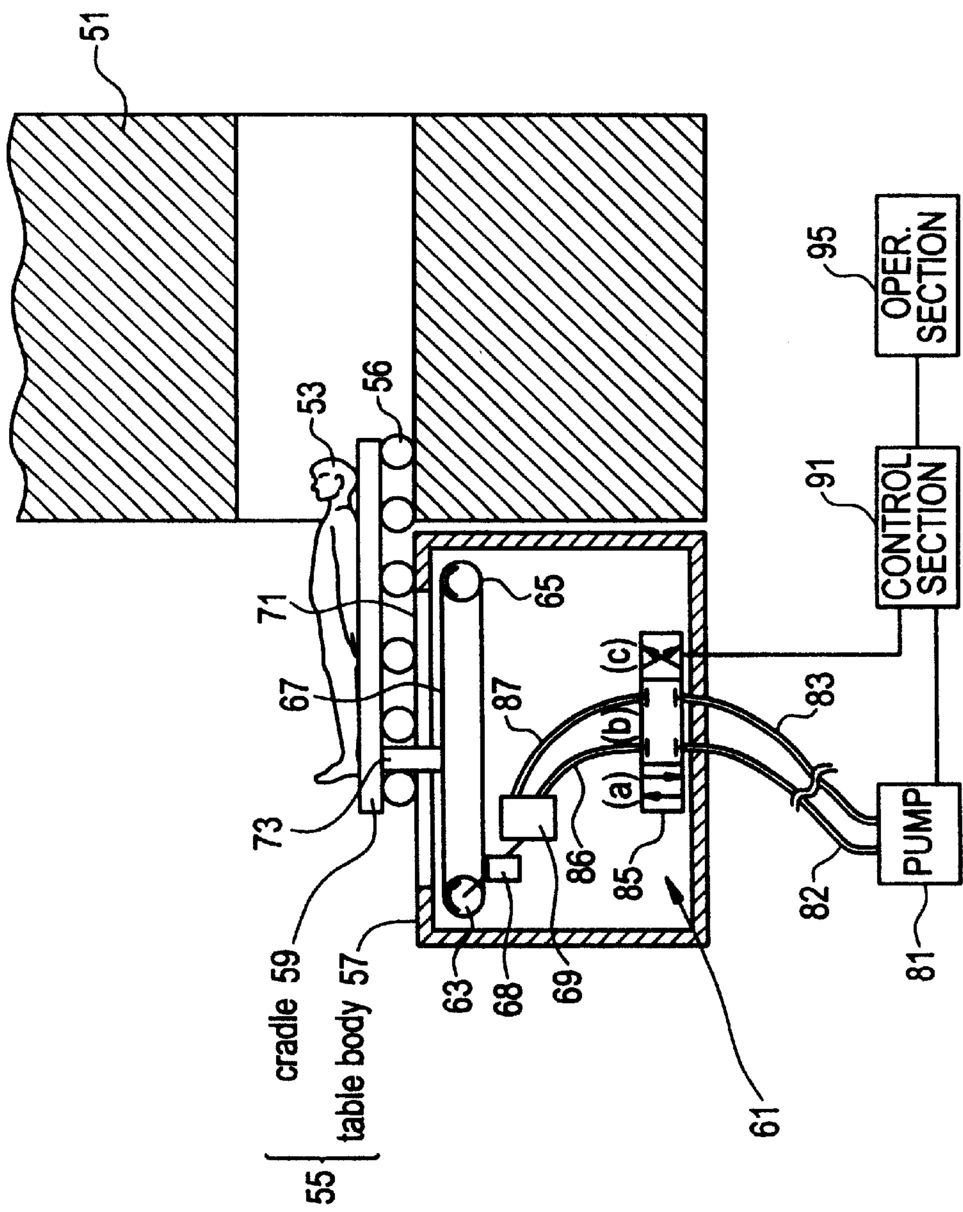
FIG. 1 illustrates configuration of a first embodiment of the present invention.

FIG. 1 illustrates configuration of a first embodiment of an MR apparatus in accordance with the present invention.

In the drawing, a table 55 for carrying an object under study 53 into a magnet 51 is generally divided into a table body 57 and a cradle 59 attached movably on the table body 57 using rollers 56, on which the object under study 53 is rested.

The table body 57 is provided therein with driving means 61 for driving the cradle 59.

The driving means 61 is comprised of two pulleys 63 and 65, a belt 67 engaged around the pulleys 63 and 65, a rotary hydraulic motor 69 that serves as a driving source for rotatively driving the pulley 63 in forward and reverse directions, a connecting member 73 for connecting the cradle 59 and the belt 67 through a slit 71 opened through an upper surface of the table body 57.

In this embodiment, since the hydraulic motor 69 by itself does not provide a sufficient accuracy, the hydraulic motor

69 and the pulley 63 are connected via a reduction mechanism 68, which employs a gear train having a large reduction ratio.

Specifically, the hydraulic motor 69 has an error (about ±20°), and if the pulley 63 is directly driven by the hydraulic motor 69 without the reduction mechanism 68, the cradle 59 has a positional accuracy of ±40 mm. On the other hand, if the pulley 63 is driven via the reduction mechanism 68, the cradle 59 has a positional accuracy of the order of ±2 mm.

Since the use of the reduction mechanism 68 having a large reduction ratio reduces the moving speed of the cradle 59 and exerts too large driving force, a high-rotation low-torque motor was employed as the hydraulic motor 69.

A hydraulic pump 81 generates hydraulic pressure. The outlet of the hydraulic pump 81 is connected with one end of a hydraulic hose 82, and the inlet of the hydraulic pump 81 is connected with one end of a hydraulic hose 83. The respective other ends of the hydraulic hoses 82 and 83 are connected to a solenoid-operated directional control valve 85, and the directional control valve 85 and the hydraulic motor 69 are connected by hydraulic hoses 86 and 87.

The directional control valve 85 of the present embodiment can be switched among three states: states (a) and (c) between which the flow directions are opposite, and a state (b) in which the flow is cut off.

Reference numeral 91 designates a control section for controlling the directional control valve 85 and the hydraulic pump 81 and reference numeral 95 designates an operating section for a human operator to supply commands to the control section 91.

Figure 2:
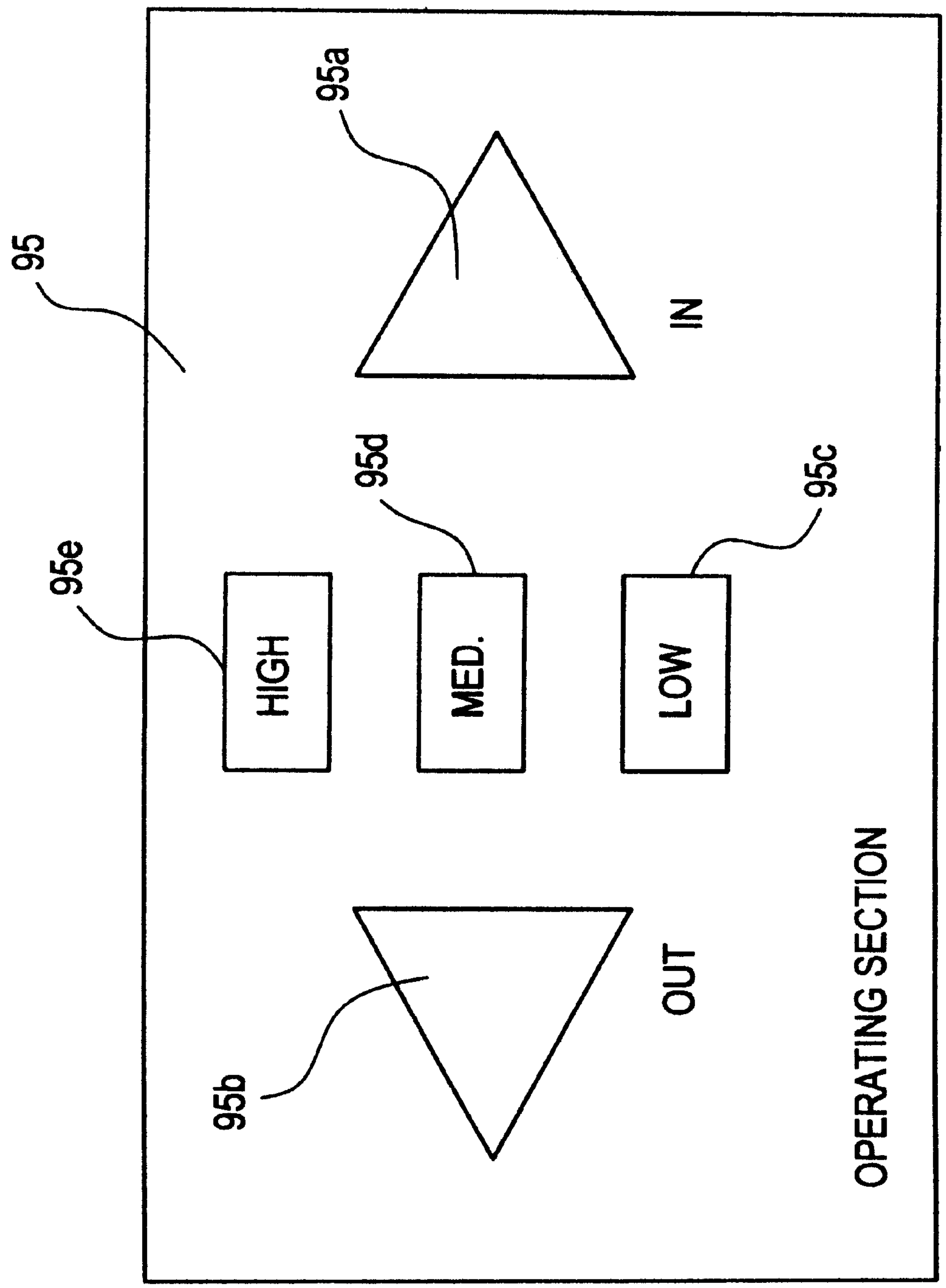
FIG. 2 illustrates the operating section in FIG. 1.

The operating section 95 is provided with an IN switch 95*a* for moving the cradle 59 toward inside of the magnet 51 (in an IN direction), an OUT switch 95*b* for moving the cradle 59 away from the magnet 51 (in an OUT direction), and low-, medium- and high-speed mode switches 95*c*, 95*d* and 95*e* for selecting the moving speed of the cradle 59, as shown in FIG. 2.

Now the operation of the above configuration will be described.

The directional control valve 85 is normally in the (b)-position, i.e., in a valve-shut state.

The human operator turns either of the low-, medium- or high-speed mode switch 95*c*, 95*d* or 95*e* on the operating section 95 ON to select the moving speed of the cradle 59.

At this time, the low-speed mode switch 95*c* is selected when the cradle 59 is to be accurately stopped at a specific position, the medium-speed mode switch 95*d* is selected when the cradle 59 is to be fed at a normal speed, and the high-speed mode switch 95*e* is selected when the cradle 59 is to be fed rapidly.

The control section 91 changes the rotation speed of the hydraulic pump 81 according to the speed mode switch that is turned ON, to vary the discharge flow rate from the pump 81. Specifically, when the low-speed mode switch 95*c* is turned ON the flow rate is low, when the medium-speed mode switch 95*d* is turned ON the flow rate is medium, and when the high-speed mode switch 95*e* is turned ON the flow rate is high.

Next, when the IN switch 95*a* on the operating section 95 is turned ON, the control section 91 switches the directional control valve 85 to the (a)-position, and drives the hydraulic pump 83 at a rotation speed according to the speed mode switch selected.

The hydraulic fluid discharged from the hydraulic pump 83 enters the hydraulic motor 69 via the directional control valve 85 in the (a)-position, causing the hydraulic motor 69 to be rotated in the forward direction. The forward rotation of the hydraulic motor 69 rotates the pulley 63 in a direction indicated by arrow, moving the belt 67 and the cradle 59 to carry the object under study 53 toward inside of the magnet 51 (in the IN-direction).

When the object under study 53 is carried in to a desired position, the operator releases the ON state of the IN switch 95*a* on the operating section 95.

Then, the control section 91 restores the directional control valve 85 to the (b)-position, and stops driving the hydraulic pump 83. By moving the directional control valve 85 to the (b)-position, or turning it into the shut state, and stopping driving the hydraulic pump 83, the forward rotation of the hydraulic motor 69 is stopped, also stopping moving the cradle 59. Next, when the operator turns the OUT switch 95*b* on the operating section 95 ON, the control section 91 switches the directional control valve 85 to the (c)-position, and drives the hydraulic pump 83.

The hydraulic fluid discharged from the hydraulic pump 83 enters the hydraulic motor 69 via the directional control valve 85 in the (c)-position, causing the hydraulic motor 69 to be rotated in the reverse direction. The reverse rotation of the hydraulic motor 69 rotates the pulley 63 in the direction reverse to that indicated by arrow, moving the belt 67 and the cradle 59 to carry the object under study 53 out of the magnet 51 (in the OUT-direction).

When the object under study 53 is carried out to a desired position, the operator releases the ON state of the OUT switch 95*b* on the operating section 95.

Then, the control section 91 restores the directional control valve 85 to the (b)-position, and stops driving the hydraulic pump 83. By moving the directional control valve 85 to the (b)-position, or turning it into the shut state, and stopping the hydraulic pump 83, the reverse rotation of the hydraulic motor 69 is stopped, also stopping moving the cradle 59.

According to the above configuration, by using the hydraulic motor 69 as means for driving the cradle 59, noises which adversely affect a captured image are not generated during driving of the cradle 59.

Therefore, moving of the cradle 59 and scanning can be simultaneously performed, and an imaging time can be reduced in imaging an extended region of the object under study 53.

Moreover, real-time display is allowed while moving an object under study, as in X-ray fluoroscopic examination.

Although the explanation has been made on the reduction mechanism 68 employing a gear train, it may alternatively employ belt pulleys.

Second Embodiment

Figure 3:
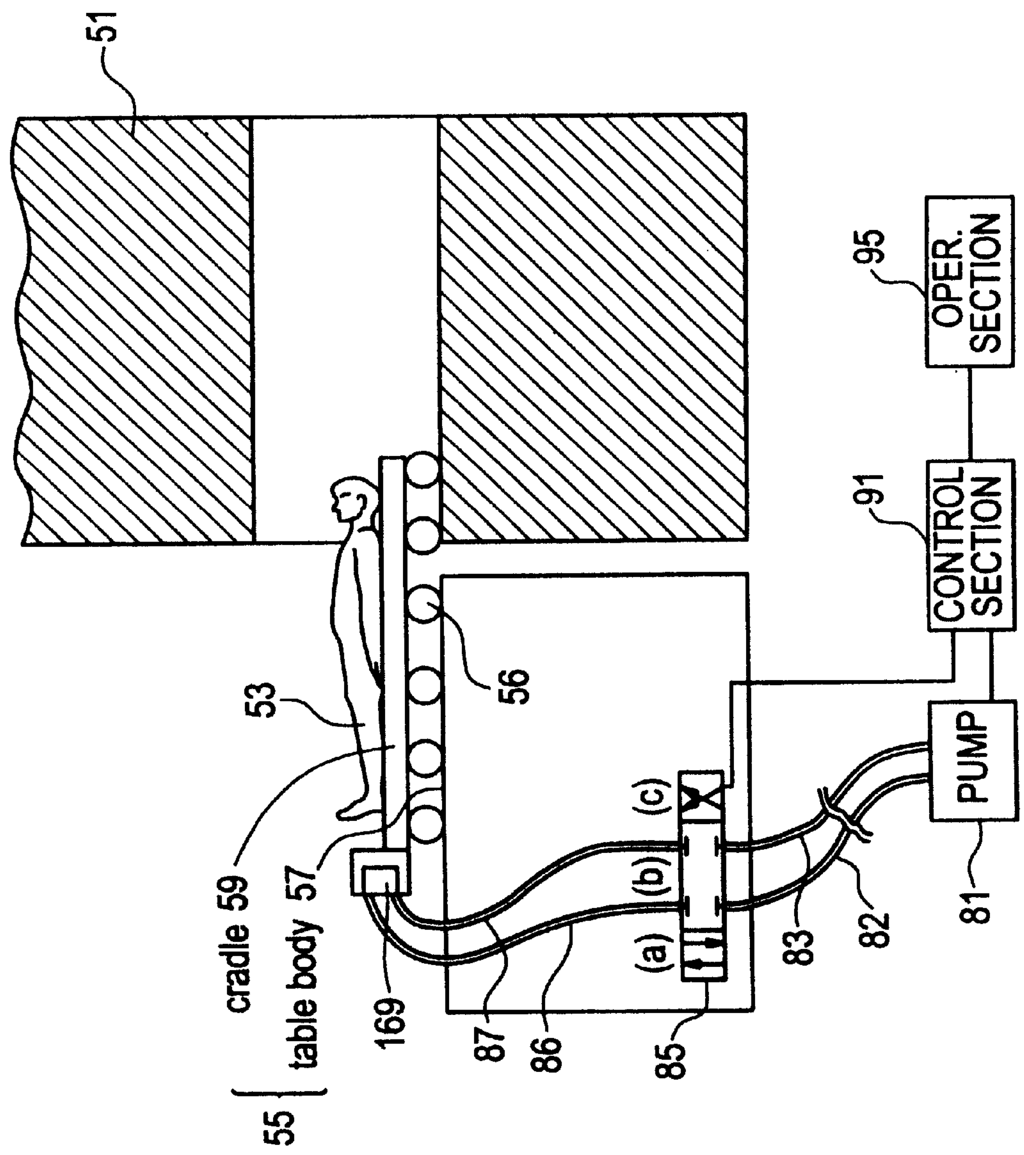
FIG. 3 illustrates configuration of a second embodiment of the present invention.

FIG. 3 illustrates configuration of a second embodiment of the MR apparatus. It should be noted that parts identical to those shown in FIG. 1 are designated by identical reference symbols in FIG. 3, and redundant explanation will be omitted.

A difference between this embodiment and the first embodiment consists in a hydraulic motor 169. Specifically, the hydraulic motor 169 of this embodiment is disposed in the cradle 59 to directly drive the rollers 56.

Moreover, a non-magnetic material is used for all the components constituting the hydraulic motor 169. According to such configuration, by using the hydraulic motor 169 made of a non-magnetic material as means for driving the cradle 59, the hydraulic motor 169 can be accurately driven even if it is placed within a high-strength magnetic field generated by the magnet 51, and the hydraulic motor 169 does not adversely affect a captured image.

Therefore, a mounting position for a driving source, or the hydraulic motor 169, is not restricted.

Moreover, by using the hydraulic motor 169, noises which adversely affect a captured image are not generated during driving of the cradle 59.

Accordingly, moving of the cradle 59 and scanning can be simultaneously performed, and an imaging time can be reduced in imaging an extended region of the object under study 53.

Moreover, real-time display is allowed while moving an object under study, as in X-ray fluoroscopic examination.

It should be noted that the present invention is not limited to the embodiments described above. While the explanation has been made on the table 55 that carries the object under study 53 into and out of the magnet 51 in the above embodiments, the present invention apply to a table that not only carries the object under study 53 into and out of the magnet 51, but also moves the object under study 53 in the right and left directions.

Many widely different embodiments of the invention may be configured without departing from the spirit and the scope of the present invention. It should be understood that the present invention is not limited to the specific embodiments described in the specification, except as defined in the appended claims.

What is claimed is:

1. A table arrangement comprising:

a cradle having a horizontal extended top surface movable horizontally and a plurality of roller means disposed on a bottom surface thereof;

a table body having a top surface on which said plurality of roller means are positioned and having an extended slit therein;

a belt contained within said table body;

pulley means contained in said table body for rotating said belt;

a connecting member disposed in said extended slit in said top surface of said table body and connecting said cradle with said belt so that movement of said belt moves said cradle; and driving means for driving said pulley to rotate said belt and thereby move said connecting means and said cradle.

2. The arrangement of claim 1, wherein said driving means utilizes gas pressure or liquid pressure.

3. The arrangement of claim 2, wherein said gas or liquid pressure is of a gas or liquid which is incompressible.

4. The arrangement of claim 1, wherein said driving means comprises a hydraulic motor and a reduction gear connected to said pulley means.

5. The arrangement of claim 4, wherein said driving means further comprises a source of fluid, and means for supplying said fluid to said hydraulic motor under control of a control means.

6. The arrangement of claim 5, wherein said fluid is gas.

7. The arrangement of claim 1, wherein said driving means comprises a non-magnetic material.

8. The arrangement of claim 1, further comprising a control means for controlling direction and speed of said driving means.

9. The arrangement of claim 1, further comprising an MRI apparatus including means for supplying a magnetic field, wherein said cradle is moved horizontally into said magnetic field.

10. A table arrangement comprising:

a cradle having a horizontal extended top surface and movable horizontally and a plurality of roller means disposed on a bottom surface thereof;

a table body having a top surface on which said plurality of roller means are disposed;

driving means for causing said plurality of roller means of said cradle to move said cradle horizontally on top of said top surface of said table body, said driving means comprising a hydraulic motor connected directly to said plurality of roller means; and control means for controlling said driving means, said control means comprising means for supplying energy to said hydraulic motor and means for controlling speed and direction of supply of such energy.

11. The arrangement of claim 10, wherein said hydraulic motor utilizes gas pressure or liquid pressure.

12. The arrangement of claim 11, wherein said gas or liquid pressure is of a gas or liquid which is incompressible.

13. The arrangement of claim 10, wherein said energy is a fluid.

14. The arrangement of claim 13, wherein said fluid is a gas.

15. The arrangement of claim 10, wherein said driving means comprises a non-magnetic material.

16. The arrangement of claim 12, further comprising an MRI apparatus including means for supplying a magnetic field, wherein said cradle is moved horizontally into said magnetic field.

* * * * *